United States Patent [19]

Wilms et al.

[11] Patent Number: 5,663,781
[45] Date of Patent: Sep. 2, 1997

[54] APPARATUS FOR THE EXAMINATION OF OBJECTS AND THE DETERMINATION OF TOPOGRAPHY

[75] Inventors: Karl-Heinz Wilms, Emmering; Ulrich Klingbeil; Andreas Plesch, both of München, all of Germany

[73] Assignee: G. Rodenstock Instrumente GmbH, Ottobrunn-Riemerling, Germany

[21] Appl. No.: 111,969

[22] Filed: Aug. 26, 1993

Related U.S. Application Data

[63] Continuation of Ser. No. 873,980, Apr. 27, 1992, abandoned, which is a continuation of Ser. No. 473,935, Feb. 28, 1990, abandoned.

[30] Foreign Application Priority Data

Jun. 29, 1988 [DE] Germany ............... 38 21 974.3
Oct. 8, 1988 [DE] Germany ............... 38 34 314.2
Oct. 8, 1988 [DE] Germany ............... 38 34 293.6

[51] Int. Cl.$^6$ .................... A61B 3/14; A61B 3/10
[52] U.S. Cl. ................ 351/206; 351/211; 396/14
[58] Field of Search ................... 351/206, 212, 351/214, 221, 211; 354/62

[56] References Cited

PUBLICATIONS

Device for producing images of an object, and in particular for observing the rear region of the eye. Feuerstein et al. Germany, OLS No. 88-3, 396.

*Primary Examiner*—Hung X. Dang
*Attorney, Agent, or Firm*—Antonelli, Terry, Stout & Kraus, LLP.

[57] ABSTRACT

Disclosed is an apparatus for examining objects having an illumination light source, the light of which can be focussed on the part of the object to be examined, a scanning device, which generates a scanning movement of the light beam from the illumination light source over the section to be examined and which is provided with beam-deflecting and beam-imaging optical elements, a sensor device, which receives the light reflected from said section to be examined, and an evaluation and synchronization unit, which produces an image of said section to be examined from the time-sequential output signal from said sensor device. The invented apparatus is distinguished by the fact that the optical axis of the examination and/or illumination beam can be shifted in a plane of said pupils in order to generate a stereoscopic image, and that the images produced with varying positions of the optical axes can be overlapped in order to produce a stereo image.

24 Claims, 4 Drawing Sheets

APPARATUS FOR THE EXAMINATION OF OBJECTS AND THE DETERMINATION OF TOPOGRAPHY

This is a continuation of application Ser. No. 07/873,980, filed Apr. 27, 1992, now abandoned which is a continuation of application Ser. No. 07/473,935, filed Feb. 28, 1990 now abandoned.

TECHNICAL FIELD

The present invention relates to an apparatus for the examination of objects, with which the construction of the image occurs by means of a "scanning process" and, in particular, to an apparatus for examining the fundus oculi.

STATE OF THE ART

A difficulty in examining the posterior portions of the eye is, by way of illustration, that the illumination and the examination have to be conducted through the pupil and the optically often not clear anterior media of the eye, in which reflexes occur and which cause aberrations.

For some time, therefore, it has been recommended to employ scanning devices that do not illuminate large areas of the posterior portions of the eye, but scan the fundus oculi with as small as possible an illumination beam and note the reflected light in correlation to the scanning sequence instead of using conventional fundus cameras. Reference with regard to this is made, by way of illustration, to "The Foundations of Ophthalmology", Vol. 7, pp. 307/308, 1962, U.S. Pat. No. 4 213 678, Japanese patent publications 61-5730 and 50-138822, and EP-A-0145 563.

Although the aforegoing apparatuses for examining objects and, in particular, for examining the posterior portions of the eye have the advantage that, due to the "scanning principle", an image of the posterior portions of the eye is yielded that is largely free of aberrations, which, by way of illustration, are caused by the unclear anterior media of the eye, however, such an image, unlike the image delivered by other known devices, by way of illustration by slit-lamp microscopes, is not a stereo image.

Moreover, it is not possible to assess the image, by way of illustration, displayed on a monitor quantitatively. Thus, it is not possible to determine, by way of illustration, the topography of the fundus oculi with the aforementioned apparatuses.

DESCRIPTION OF THE INVENTION

The object of the present invention is to provide an apparatus operating by the "scanning principle", which permits determining the topography of the object to have an image made of and which, in particular, is able to deliver a stereo image and, in addition to the image of the fundus oculi, is able to deliver quantitative data on the structure of the fundus oculi.

A solution to the aforegoing object in accordance with the present invention and its further embodiments is set forth in the claims hereto.

Strikingly, one solution to the aforegoing object of the present invention is successful on the basis that it proceeds from an apparatus for examining objects, i.e. from an apparatus operating with an illumination light source and a scanning device.

The afore-described apparatus is further improved in accordance with the present invention in that for determining the topography of the object at least two images of the object can be taken time-sequentially or simultaneously with off-set pupils of the illumination and/or detection beam path and that the evaluation and synchronization unit couples the images taken with different pupil positions.

In this case, it is, in particular, possible to employ more than two overlapping pupils and to couple the images taken from different directions of vision with a redundant algorithm in such a manner that more reliable data on the topography, by way of illustration, of the fundus oculi, are received.

Naturally, it is also possible, in order to produce a stereoscopic image, to only take two images and that for this purpose the optical axis of the examination and/or illumination light beam can be shifted in a plane conjugate to the plane of the pupils and that the images produced with the different position of the optical axis are super-imposed in order to produce a stereo image.

The stereo effect can be substantially increased if the invented measures taken for producing a stereo image act on both the illumination light beam and on the examination light beam.

An element of the present invention is that the afore-described shifting of the optical axis of the examination and/or illumination light beam occurs in a plane conjugate to the plane of the pupils, by way of illustration, by a parallel shifting of the optical axis by means of an Allen separator or by tilting an element of the optical system of the invented apparatus.

By way of illustration, an exit window or some other optical element that is conjugate to the plane of the image may be tiltable.

Furthermore, shutters may be provided before the sensor for switching between the different positions of the sensing pupils. At least two spaced sensors may be provided for realizing the shifting of the sensing pupils or the shifting of the illumination pupil and of the sensing pupil may occur collectively.

Another solution to the object of the present invention is achieved with an apparatus operating with a confocal beam path, respectively by the "double scanning principle", thus yielding a stationary signal light beam.

An element of the present invention is that at least one lens element having a cylindrical effect and a quadrant sensor, which is arranged in the center plane of both focus planes of the cylinder-lens element, are provided. The evaluation and synchronization unit assesses the distribution of intensity on the quadrant sensor. The invented apparatus thus operates as follows:

The astigmatic system provided in the sensing beam path delivers two line foci, which are spaced at a specific axial distance, in the meridional, respectively sagittal, plane of the image. As the quadrant sensor is situated in the center between the two image planes, if the scanning laser beam is focussed precisely on the reflecting surface, the two line foci are spaced the same distance before and behind the quadrant sensor, thereby yielding in this case a circular distribution of intensity in the sensor plane.

On the other hand, if the scanned surface is situated outside the focus plane of the scanning laser beam, depending on the size of the deviation, an oval distribution of intensity, the orientation of which depending on the direction of the deviation, i.e. whether or not the focus plane of the scanning laser beam lies before or behind the fundus oculi, and its eccentricity depends on the amount of the deviation, is yielded on the quadrant sensor.

This asymmetry can be verified by means of suitable arithmetic coupling of the four quadrants of the quadrant sensor.

In this manner the output signal of the quadrant sensor delivers depth data, which can either be utilized for compensating for the focal deviation, i.e. for realizing an autofocus system, or also for representing data on the topography of the fundus oculi.

This data can either be derived from the shifting, required for focussing, of the movable element provided in the illumination beam path detected, by way of illustration, by an, as such known, path sensor, or from the eccentricity of the signal on the quadrant sensor.

Simultaneously, the overall reflectivity of the scanned object can be determined by additive coupling of the four sectors of the quadrant sensor, thus a normal reflexion image can be yielded.

The invented apparatus therefore delivers, in addition to an image of the fundus oculi, information on the topography of the fundus oculi, i.e. information on the 3-dimensional formation of the fundus oculi.

The measuring area and the depth resolution of the invented apparatus can easily be adapted to the respective conditions by means of appropriate selection of the focal distance of the spherical lens elements and the astigmatic lens elements in the sensing beam path.

A BRIEF DESCRIPTION OF THE DRAWING

The present invention is made more apparent in the following section using preferred embodiments with reference to the accompanying drawing, depicting in:

FIG. 1 a top view of an invented apparatus,

FIG. 2a a section of an invented apparatus with an Allen separator,

FIG. 2b the corresponding separation of the pupil,

FIG. 3 the shutters in the plane of the pupils when spaced pupils are employed, and FIG. 4a the beam path when a scanning-stereoscopic image is taken, and FIG. 4b the corresponding separation of the pupil, FIG. 5a and 5b separations of the pupils when utilizing more than two pupils, and FIG. 6 another embodiment of the invented apparatus.

DESCRIPTION OF PREFERRED EMBODIMENTS

Figure 1:
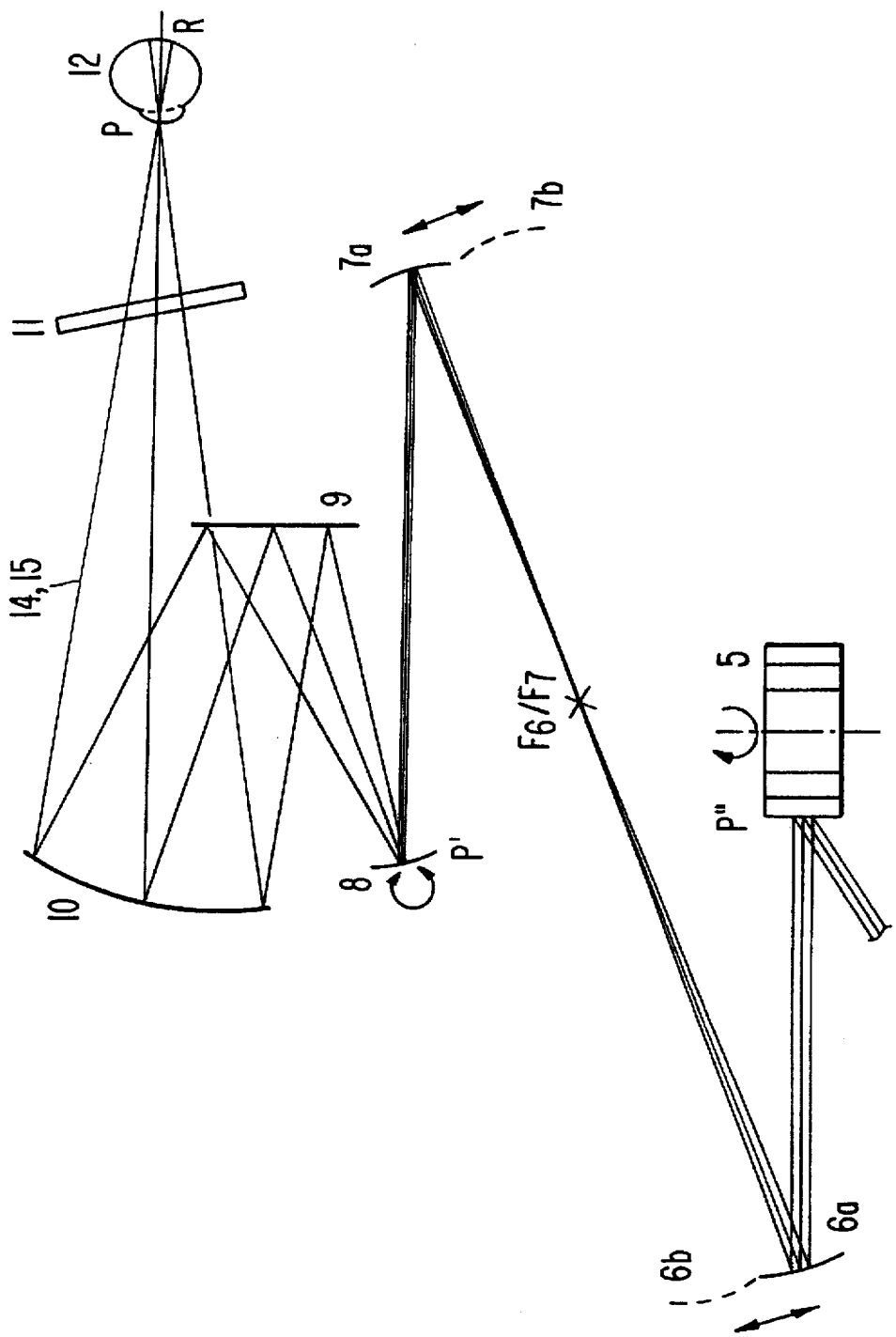

The invented apparatus depicted in a section in FIG. 1 is provided with a not depicted illumination light source, by way of illustration a laser, and an also not depicted sensor device, the output signal of which is assessed by an evaluation and synchronization unit and, by way of illustration, is displayed on a monitor. In the illustrated preferred embodiment, both the illumination light beam 14 and the light beam 15 coming from the fundus oculi "run" via a deflection device.

The light beam 14 from the laser is deflected in a horizontal direction (perpendicular to the plane of the drawing) by a first deflection element (horizontal scanner), which, in the illustrated preferred embodiment, is a rotating polygonal mirror 5. The beam fanning out in the horizontal plane runs through mirror system 6 and 7 and hits a second deflection element (vertical scanner), which, in the illustrated preferred embodiment, is an oscillating, respectively a galvanometer, mirror 8. Behind mirror 8, the bundle of rays has a "rectangular" cross-section. Following deflection at a plane mirror 9, its image is projected by a concave mirror 10 via an element 11, described later herein, onto the eye 12 to be examined. The reflected ray of light 15 runs through the mentioned elements in reverse order and is detected behind the horizontal deflecting element 5 by a not depicted sensor after prior separation of the illumination and the examination light paths.

An element of the present invention is that it is based on the following fundamental concepts:

During the "scanning process", the examination direction and thus the stereo parallaxe is essentially determined by confining the illumination on a small portion of the pupil with the collimated laser beam 14.

Figure 2A:
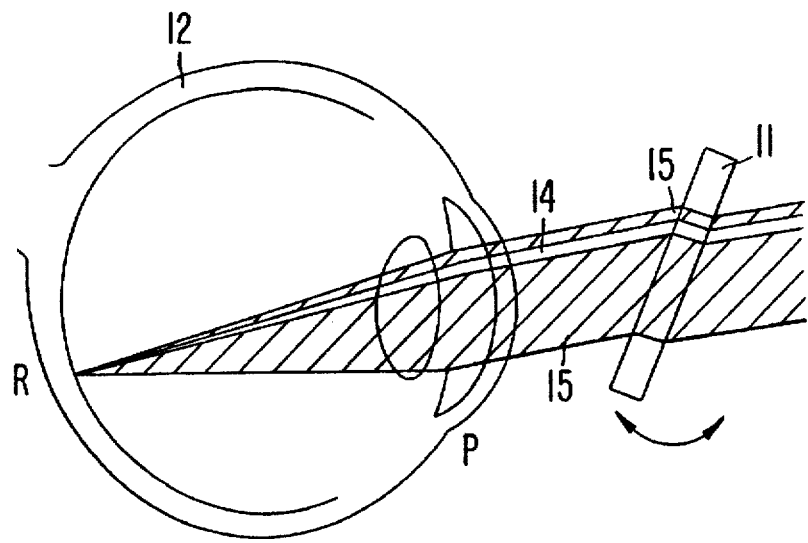
Figure 2B:
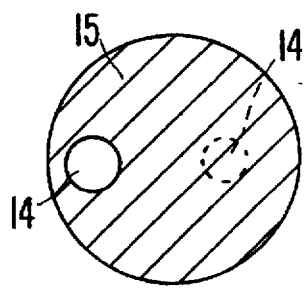

FIG. 2a shows that shifting the laser beam 14 parallel relative to the pupil P effects a change in the orientation of the incidence of light on the fundus oculi, thereby yielding stereoscopic variances in the image. FIG. 2b shows the "separation of the pupil" in the plane of the pupil P between the illumination light beam 14, the beam 14' in the conjugate stereo position and the examination beam 15.

Technically such a separation of the pupil, by way of illustration, can be realized by means of shifting the optical axis of the system parallel in relation to the pupil P, e.g., by means of an Allen separator, by means of tilting the exit window 11 or by means of tilting one of the mirrors of the optical system.

The tilted mirror should be conjugate as possible to the plane R of the image and as little conjugate as possible to the plane P of the pupil in such a manner that it can develop the desired optical effect. A mirror fulfilling these conditions is, by way of illustration, mirror 9.

With the invented apparatus, in which both the illumination light beam 14 and the ray of light 15 reflected from the fundus oculi are guided via the x/y scanning elements, the stereo effect can be augmented by combining the illumination stereo effect with an "examination stereo effect":

The illumination stereo effect may, in this case, be achieved with means known from the classical ophthalmoscopes, the combination of "both stereo effects" corresponding to an enlargement of the stereo base by the diameter of the pupil.

Figure 3:
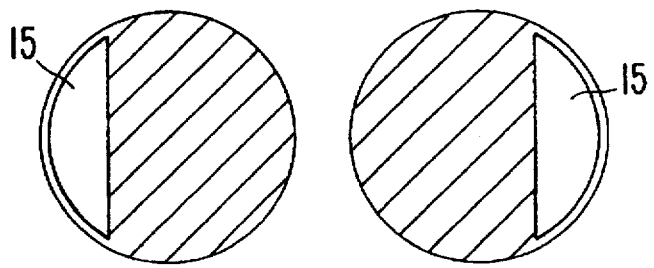

For this purpose, both the stereo images are taken sequentially. While the first image is taken, the illumination beam must lie on the one side of the pupil, while the second stereo image is taken on the other side of the pupil (FIG. 3). Between taking the images, switching must occur as fast as possible by means of, by way of illustration, the means known from the description of FIG. 2. The time-sequential stereo images are subsequentially accordingly superimposed electronically or assessed with an electronical image evaluation.

Simultaneous with shifting the position of the illumination light beam 14 in the pupil plane P, the position of the sensing pupil plane is shifted counter to it—as shown in FIG. 3. This can be achieved, by way of illustration, by means of an interchangeable set of shutters before the detection sensor in a plane conjugate to the pupil P or by means of a set of sensors arranged accordingly, which are selectively synchronized to deliver the signal of the image.

Furthermore, a stereo separation may, of course, also be conducted in the sensing bee path in a plane conjugate to the plane of the pupil, by means known in the are, making it possible to take stereo images simultaneously.

Figure 4A:
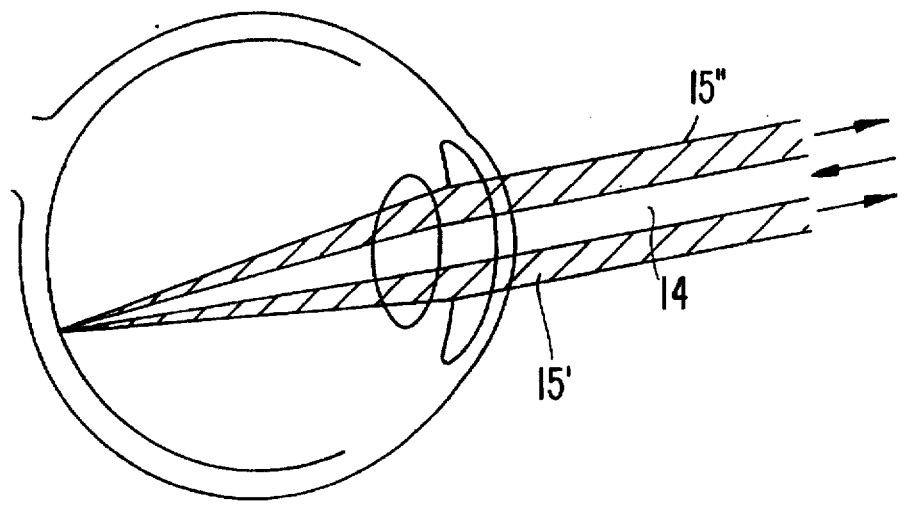

FIG. 4a shows the corresponding illumination beam path 14 and the two examination beam path 15' and 15".

Figure 4B:
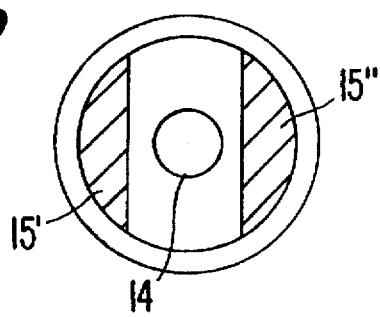

FIG. 4b shows the realized corresponding separation of the pupil, by way of illustration, by means of a respective shutter.

Two simultaneously operating sensors are required for "taking stereo images" simultaneously, which examine off-set subranges of the pupil P and, if need be, a stereo prism with a shutter or the like, which separates the pupil. In this case, however, the stereo base is confined by the diameter of the pupil so that the stereo parallaxe and the stereo separation depend on the degree to which the two subranges can be off-set from each other.

Figure 5A:
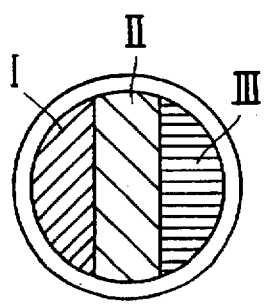
Figure 5B:
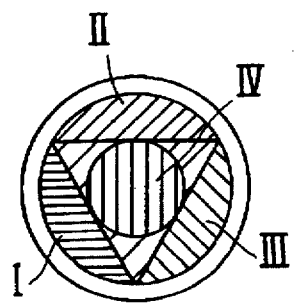

The arrangement of three, respectively four, overlapping pupils I–III, respectively I–IV, is shown in FIGS. 5a and 5b. The pupils are formed in such a manner that the centers of gravity of the pupils defined in the respective beam paths are off-set.

In each case one of the images taken, the pupil position of which assumes a central position in relation to the others, serves as a reference for the assessment. In this way, a "multi-image stereoscopy" is yielded, which has the advantage that the results are more reliable and the evaluation algorithms are simpler.

Moreover, in each case the half-images can be assessed subjectively or be determined by means of image analysis and the topography can be calculated with a computer.

Figure 6:
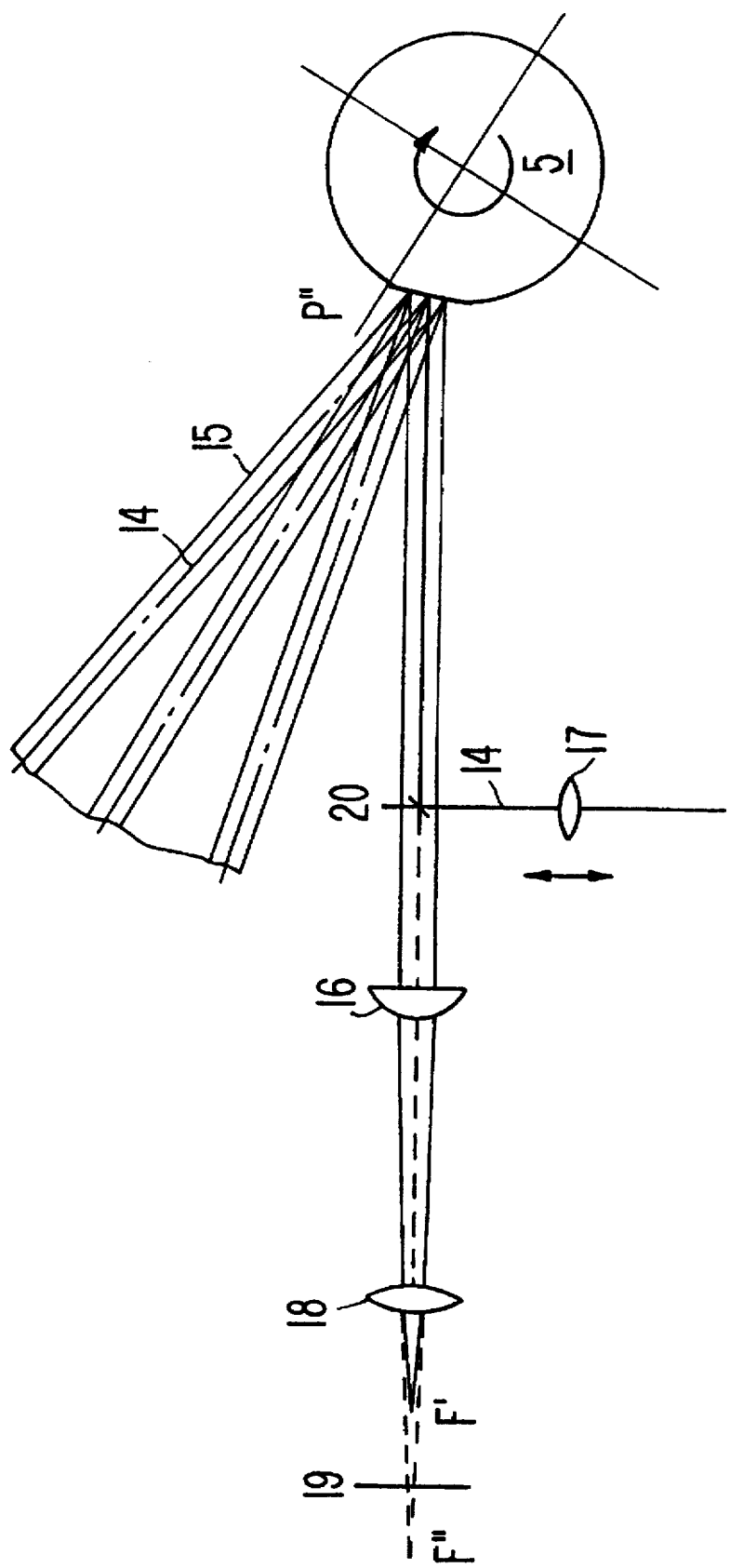

FIG. 6 shows another preferred embodiment of the present invention, of which only the portion that is lying before the horizontal scanner 5 is depicted. The portion of the invented apparatus lying "behind scanner 5" may be formed according to FIGS. 1 to 5 or in a conventional manner.

In illumination beam path 14 before, respectively in, examination beam path 15 behind deflection element 5 is arranged a divider mirror 20 for both beam paths 14 and 15, which in the illustrated preferred embodiment leads to an inverted Gullstrand pupil without the intention of limiting the scope of the overall inventive concept. Behind divider mirror 20 in the sensing beam path 15 are provided a lens element 16 with a cylindrical effect, a lens element 18 with a rotational-symmetrical effect and a quadrant sensor 19. The quadrant sensor 19 is arranged in the central plane of both focal planes F' and F" of the cylinder-lens element 16. The not depicted evaluation and synchronization unit assesses the distribution of intensity on the quadrant sensor. Furthermore, a movable lens element 17 is provided in the illumination beam path 14 "before" the divider mirror 20 in direction of the arrow.

Thus, the invented apparatus operates as follows:

The astigmatic system 16 provided in the sensing beam path delivers two line foci, which are spaced at a specific axial distance, in the meridional, respectively sagittal plane F', respectively F", of the image, which are spaced at a specific axial distance. As quadrant sensor 19 is situated in the center between the two line foci when the scanning laser beam is focussed precisely on the reflecting surface, the same distance before and behind the quadrant sensor. In this manner, a circular distribution of intensity is yielded in the plane of the sensor. On the other hand, if the scanned surface is situated outside the focus plane of the scanning laser beam, depending on the size of the deviation, an oval distribution of intensity, the orientation of which depending on the direction of the deviation, i.e. whether or not the focus plane of the scanning laser beam lies before or behind the fundus oculi, and its eccentricity depends on the amount of the deviation, is yielded on the quadrant sensor 19.

The asymmetry can be proven by means of suitable arithmetic coupling of the four quadrants of the quadrant sensor.

In this manner, the output signal of the quadrant sensor delivers depth data, which can either be utilized for compensating for the focal deviation, i.e. for realizing an autofocus system, or also for representing data on the topography of the fundus oculi.

These data can either be derived from the shifting, required for focussing, of the movable element 17 provided in the illumination beam path detected, by way of illustration, by an, as such known, path sensor, or from the eccentricity of the signal on the quadrant sensor.

Simultaneously, the overall reflectivity of the scanned object can be determined by additive coupling of the four sectors of the quadrant sensor, thus a normal reflexion image can be yielded.

The measuring area and the depth resolution of the invented apparatus can easily be adapted to the respective conditions by means of appropriate selection of the focal distance of the spherical lens elements and the astigmatic lens element in the sensing beam path.

Simultaneously, the overall reflectivity of the scanned object can be determined by additive coupling of the four sectors of the quadrant sensor, thus a normal reflexion image can be yielded.

In this manner, the invented apparatus delivers, in addition to an image of the fundus oculi, information on the topography of the fundus oculi, i.e. information on the 3-dimensional formation of the fundus oculi.

Furthermore, the output signal can be utilized for focussing and thus for improving the resolution of the invented apparatus.

The measuring area and the depth resolution of the invented apparatus can easily be adapted to the respective conditions by means of appropriate selection of the focal distance of the spherical lens elements 18 and the astigmatic lens element 16 in the sensing beam path.

Moreover, the invented apparatus can also be utilized for determining the topography of the cornea.

The present invention is described in the preceding section without the intention of limiting the overall inventive concept. In particular, the individual measures described herein may be combined with one another.

What is claimed is:

1. An apparatus for examining an object comprising:
   an illumination light source for generating an illumination light beam of a predetermined wavelength for being focused by beam-imaging optical elements along an illumination light beam path on a portion of the object to be examined;
   scanning means including beam-deflecting optical elements for generating a scanning movement of the illumination light beam over the object to be examined;
   sensing means for receiving a light reflected beam of the illumination beam reflected from the object to be examined along a reflected light beam path including a sensing beam path; and
   evaluation and synchronization means for producing an image of the object to be examined from a time-sequential output signal from the sensing means;
   wherein the illumination light source, the beam-imaging optical elements, the scanning means, the sensing means and the evaluation and synchronization means enable at least two images of the object to be simultaneously taken with off-set pupils of at least one of the illumination light beam path and the reflected light beam path and a shifted optical axis of at least one of the illumination light beam and the reflected light beam, the evaluation and synchronization means enabling coupling of the images taken with varying positions of the pupils and optical axis for determining the topography of the object.

2. An apparatus according to claim 1, wherein optical axes of illumination light beams are off-set in the plane of the pupils for individual images.

3. An apparatus according to claim 1, wherein the optical axis of at least one of the illumination light beam and the reflected light beam is shifted in a plane of the pupils for generating a stereoscopic image, and images produced with varying positions of the optical axes are overlapped for producing a stereo image.

4. An apparatus according to claim 1, wherein at least one of the beam-imaging optical elements and the beam-deflecting optical elements include at least one of an Allen separator and a tiltable element for enabling a parallel shifting of the optical axis of the illumination light beam.

5. An apparatus according to claims 4, wherein the tiltable element is an exit window.

6. An apparatus according to claim 4, wherein the tiltable element is an optical element which is conjugate to the plane of the image.

7. An apparatus according to claim 1, wherein the sensing means includes shutters provided before a sensor for switching between varying positions of sensing pupils.

8. An apparatus according to claim 1, wherein the sensing means includes at least two sensors for enabling shifting of sensing pupils.

9. An apparatus according to claim 1 wherein an illumination pupil and a sensing pupil are shifted in directions counter to each other.

10. An apparatus according to claim 1, wherein more than two images are simultaneously taken.

11. An apparatus according to claim 1, further comprising means for modulating the illumination beam.

12. An apparatus according to claim 11, wherein the modulating means includes grids.

13. An apparatus according to claim 1, wherein the illumination light beam and reflected light beam are of the same predetermined single wavelength.

14. An apparatus for examining an object comprising:
an illumination light source for generating an illumination light beam for being focused by beam-imaging optical elements along an illumination light beam path on a portion of the object to be examined;
scanning means including beam-deflecting optical elements for generating a scanning movement of the illumination light beam over the object to be examined;
sensing means for receiving a light beam reflected from the object to be examined along a reflected light beam path including a sensing beam path; and
evaluation and synchronization means for producing an image of the object to be examined from a time-sequential output signal from the sensing means;
wherein the illumination light source, the beam-imaging optical elements, the scanning means, the sensing means and the evaluation and synchronization means enable at least two images of the object to be simultaneously taken with off-set pupils of at least one of the illumination light beam path and the reflected light beam path and a shifted optical axis of at least one of the illumination light beam and the reflected light beam, the evaluation and synchronization means enabling coupling of the images taken with varying positions of the pupils and optical axis for determining the topography of the object, and
wherein the beam-deflecting elements and the beam-imaging elements are disposed in both the illumination light beam path and the sensing light beam path and include a lens element having a cylindrical effect, the sensing means including a quadrant sensor arranged in the center plane of two focus planes of the lens element providing the cylindrical effect and in the sensing beam path, the evaluation and synchronization means being responsive to an output of the quadrant sensor indicative of the distribution of intensity thereon.

15. An apparatus according to claim 14, wherein at least one of the beam-imaging optical elements and the beam-deflecting optical elements includes at least one movable element provided at least in the illumination beam path, the evaluation and synchronization means enabling movement of the at least one movable element so that the distribution of intensity on the quadrant sensor is substantially circular.

16. An apparatus according to claim 15, wherein the evaluation and synchronization means enables determination of the topography of a fundus oculi as the object to be examined in accordance with an eccentricity of the distribution of intensity on the quadrant sensor and movement of the at least one movable element.

17. An apparatus according to claim 15, further comprising a lens element having a spherical effect arranged in the beam path.

18. An apparatus according to claim 14, wherein the evaluation and synchronization means enables determination of the topography of a fundus oculi as the object to be examined in accordance with an eccentricity of the distribution of intensity on the quadrant sensor and movement of the at least one movable element.

19. An apparatus according to claim 14, further comprising a lens element having a spherical effect arranged in the beam path.

20. An apparatus for examining an object comprising:
an illumination light source generating an illumination light beam of a predetermined wavelength which is focused by beam-imaging optical elements along an illumination light beam path on a portion of the object to be examined;
a scanner means including beam-deflecting optical elements generating scanning movement of the illumination light beam over the object to be examined;
a sensor receiving a reflected light beam of the illumination beam which is reflected from the object to be examined along a reflected light beam path including a sensing beam path; and
an evaluator and synchronizer producing an image of the object to be examined from a time-sequential output signal from the sensor;
the illumination light source, the beam-imaging optical elements, the scanner, the sensor and the evaluator and synchronizer being arranged so that at least two images of the object are simultaneously taken with off-set pupils of at least one of the illumination light beam path and the reflected light beam path and a shifted optical axis of at least one of the illumination light beam and the reflected light beam, the evaluator and synchronizer coupling the images taken with varying positions of the pupils and optical axis so as to determine the topography of the object.

21. An apparatus according to claim 20, wherein the beam-deflecting elements and the beam-imaging elements are disposed in both the illumination light beam path and the sensing beam path and include a lens element having a cylindrical effect.

22. An apparatus according to claim 21, wherein the sensor includes a quadrant sensor arranged in the center plane of two focus planes of the lens element providing the cylindrical effect.

23. An apparatus according to claim 22, wherein the evaluator and synchronizer is responsive to an output of the quadrant sensor indicative of the distribution of intensity thereon.

24. An apparatus according to claim 20, wherein only a single illumination light source is provided.

* * * * *